(12) United States Patent
Grodzins et al.

(10) Patent No.: US 6,424,695 B1
(45) Date of Patent: *Jul. 23, 2002

(54) SEPARATE LATERAL PROCESSING OF BACKSCATTER SIGNALS

(75) Inventors: Lee Grodzins, Lexington, MA (US); William Adams, Powell, OH (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,103

(22) Filed: Dec. 16, 1999

Related U.S. Application Data
(60) Provisional application No. 60/113,412, filed on Dec. 22, 1998.

(51) Int. Cl.[7] .............................................. G01N 23/201
(52) U.S. Cl. ............................. 378/87; 378/70; 378/86; 378/87
(58) Field of Search ............................... 378/70, 86, 87

(56) References Cited

U.S. PATENT DOCUMENTS

| | | | |
|---|---|---|---|
| 3,961,186 A | 6/1976 | Leunbach ................... 250/272 |
| 4,864,142 A | 9/1989 | Gomberg ................ 250/390.04 |
| 5,428,657 A | * 6/1995 | Papanicolopoulos et al. . 378/86 |
| 5,430,787 A | 7/1995 | Norton ......................... 378/87 |
| 5,763,886 A | 6/1998 | Schulte ...................... 250/38.1 |
| 6,081,580 A | 6/2000 | Grodzins et al. ............. 378/87 |
| 6,282,260 B1 | * 8/2001 | Grodzins ...................... 378/87 |

FOREIGN PATENT DOCUMENTS

| | | | |
|---|---|---|---|
| EP | 0261984 A2 | 3/1988 | .......... G01N/23/04 |

OTHER PUBLICATIONS

U.S. Patent application No. 09/448,721, filed Apr. 25, 2000.

* cited by examiner

Primary Examiner—Robert H. Kim
Assistant Examiner—Courtney Thomas
(74) Attorney, Agent, or Firm—Bromberg & Sunstein LLP

(57) ABSTRACT

A system and a method for determining the depth of an object with respect to a surface behind which the object is concealed. The intensity of x-rays backscattered from the object is measured by at least two backscatter detectors disposed at different positions with respect to the scattering object. The depth of a scattering source within the volume penetrated by the x-rays is derived from the ratio of scattered x-rays measured by the detectors.

9 Claims, 4 Drawing Sheets

SEPARATE LATERAL PROCESSING OF BACKSCATTER SIGNALS

The present application claims priority from U.S. Provisional Application No. U.S. Provisional Application No. 60/113,412, filed Dec. 22, 1998, which is incorporated herein by reference.

TECHNICAL FIELD

The present invention relates to x-ray inspection of containers, and, more particularly, to x-ray inspection employing the detection of backscatter radiation by means of a plurality of backscatter detectors in order to derive information including spatial and material information with respect to contents of the containers.

BACKGROUND OF THE INVENTION

It is desirable to be able to determine the presence of objects, such as contraband, weapons, or explosives, that have been concealed in an enclosure, such as luggage or a shipping container, or that are concealed behind a surface such as a wall. Additionally, it is desirable to obtain information regarding the geometrical and material characteristics of such objects. Conventional x-ray techniques provide measures either of attenuation, in the case of transmission techniques, or of scatter, in the case of scatter techniques.

Various methods of identifying a backscatter signal with a position within an illuminated enclosure employ scanned beams of x-rays, as described, for example, in U.S. Pat. Nos. 4,809,312 and 4,825,454 which are hereby incorporated herein by reference. In practice, the backscatter intensity may give only a crude measure of the atomic number of the object since the backscatter intensity is a function of several variables: the effective atomic number of the object; the object's geometry, including its distance from the x-ray source and the detectors; and the presence of material interposed between the object and the x-ray source/detector arrangement. It is desirable to obtain and process further scatter data so as to resolve a portion of the ambiguity inherent in backscatter measurements.

SUMMARY OF THE INVENTION

In accordance with one aspect of the invention, in a preferred embodiment, there is provided an inspection system for characterizing an object concealed by a concealing surface. The system has a source of penetrating radiation for emitting a beam that has an orientation and is incident upon the concealing surface at a plane of incidence. The source of penetrating radiation is characterized by a source position. The system also has a first scatter detector having a specified position with respect to the source position and beam orientation, for generating a first signal corresponding to penetrating radiation that has been scattered by the object. Additionally, the system has a second scatter detector having a field of view. The second scatter detector also has a specified position with respect to the source position and beam orientation and generates a second signal corresponding to penetrating radiation that has been scattered by the object. Finally, the system has a controller for determining an effective depth of the object with respect to the plane of incidence on the basis of at least the first and second signals.

BRIEF DESCRIPTION OF THE DRAWINGS

The foregoing features of the invention will be more readily understood by reference to the following detailed description taken with the accompanying drawings in which.

DETAILED DESCRIPTION OF PREFERRED EMBODIMENTS

Figure 1:
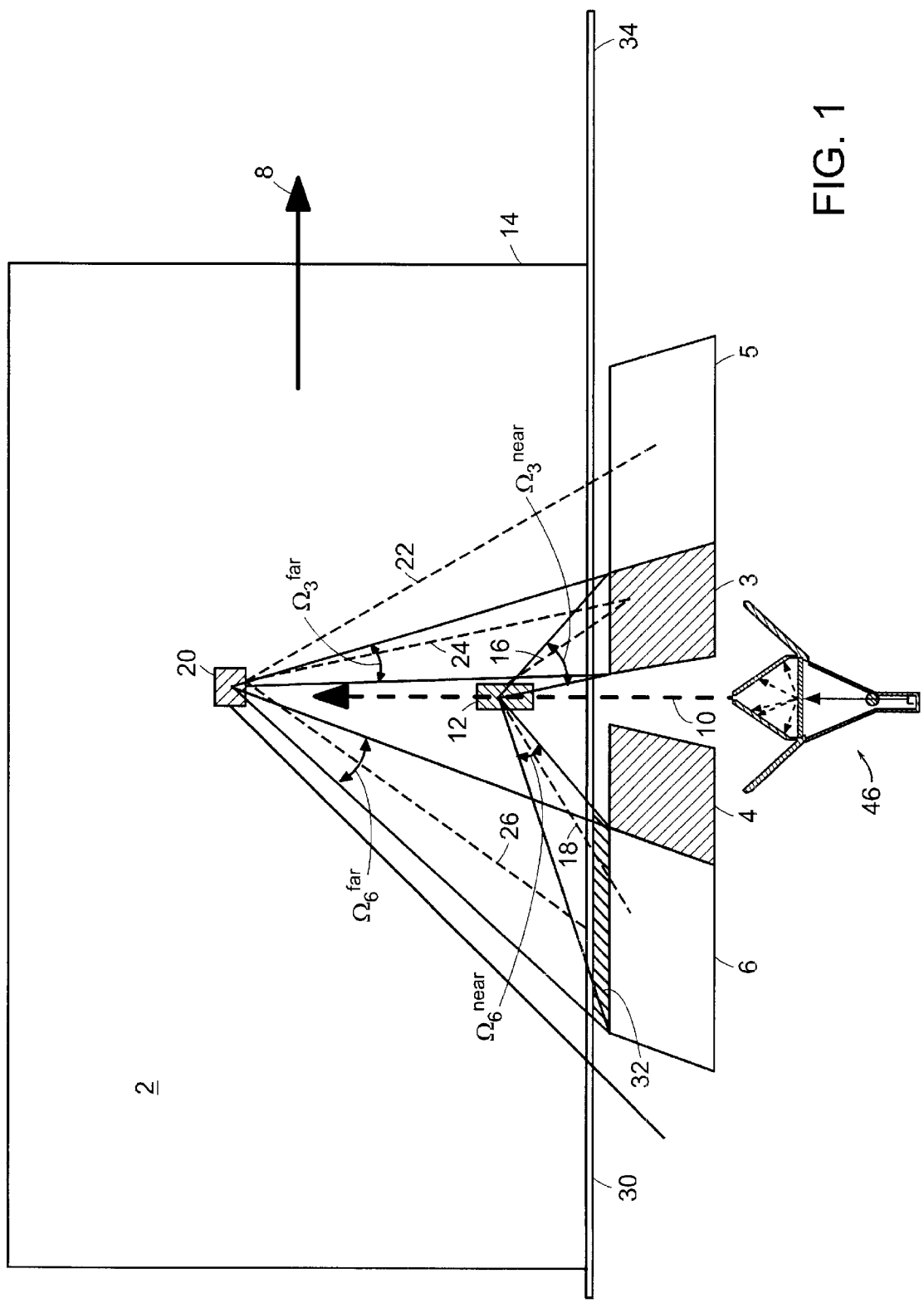
FIG. 1 depicts a schematic cross-sectional representation of an x-ray system employing multiple backscatter detectors for obtaining depth information with respect to concealed objects in accordance with a preferred embodiment of the present invention.

A principle of operation of preferred embodiment of the present invention, whereby geometrical and material information with respect to a concealed object may be derived by using multiple or segmented backscatter detectors to measure the intensity of x-rays backscattered from the object, is described with reference to FIG. 1. A beam 10 of penetrating radiation is incident upon one or more objects 12 and 20 which may be concealed from view, such as by surface 30 which may be the surface of a wall or may be a surface of an enclosure or container 14. A volume 2 posterior to surface 30 or contained within enclosure 14 may be referred to, herein, without limitation, simply as "enclosure 14." "Penetrating radiation" refers to electromagnetic radiation of an appropriate range of energy and intensity as to penetrate container 14 and objects 12 and 20, and will be referred to, without limitation, in the following description as x-ray radiation. Beam 10 will similarly be referred to, without limitation, as an x-ray beam. Beam 10 is generated by a source (not shown) of penetrating radiation which may, for example, be an x-ray tube or a radioactive source. Plane 30 tangential to a point at which beam 10 penetrates surface enclosure 14 is referred to as the "plane of incidence."

X-rays 10 are scattered by objects 12 and 20, giving rise, for example, to scattered x-ray paths 16, 18, 22, 24, and 26. Backscatter detectors 3, 4, 5, and 6 are disposed on the same side of container 14 as source 46, with detectors 3 and 5 on one side of beam 10 and detectors 4 and 6 on the opposite side of the beam. X-rays 10 are preferably in the form of a pencil beam that is raster scanned in the plane perpendicular to the line of the detectors Other shapes of beam 10 may also be employed within the scope of the present invention. Backscatter detectors may be any detectors known in the art for detection of the penetrating radiation scattered by objects 12 and 20, with the choice of particular detectors governed by design considerations with respect to a particular system and application. Backscatter detectors 3, 4, 5, and 6 may include, without limitation, an array of x-ray detectors arranged in a linear or planar configuration. The detectors may be segmented scintillators or other solid state detectors, for example, or photomultipliers or liquid scintillators which may be doped with tin or other metal. The use of cesium-iodide on PIN diodes and of room-temperature CdZnTe semiconductors are examples of detector technologies which may be employed. Energy resolution of backscatter detectors 3, 4, 5, and 6 is within the scope of the present invention and advantageously allows a determination of material characteristics of the object according to algoritms well-known in the art.

The position and relative sizes of backscatter detectors 3, 4, 5, and 6 may be chosen, in accordance with preferred embodiments of the invention, to optimize the efficiency of the system in discriminating among x-rays scattered from various selected regions of the space penetrated by beam 10, and to obtain images that enhance scattering features located at different depths into container 14. Radiation scattered from more distant scattering sources such as object 20 will be detected preferentially by exterior detectors 5 and 6 relative to interior detectors 3 and 4 since the detected flux is substantially proportional to the solid angles (depicted in projection in the plane of the paper) designated respectively as $\Omega_6^{far}$ and $\Omega_3^{far}$, subtended by the respective detectors. The collection area of exterior detectors 5 and 6 may be increased relative to the collection area of the interior detectors 3 and 4 in order to enhance the magnitude of $\Omega_6^{far}$ relative to $\Omega_3^{far}$ for the more distant scattering sources 20. By way of contrast, for nearer object 12, the ratio of solid angles (depicted in projection in the plane of the paper) designated respectively as $\Omega_6^{near}$ and $\Omega_3^{near}$, subtended by exterior detectors 5 and 6 relative to interior detectors 3 and 4, favors detection by the interior detectors.

As enclosure 14 is scanned in lateral direction 8 with respect to beam 10, whether by motion of the enclosure on a conveyor 34, or, equivalently, by motion of beam 10, the contents of enclosure 14 may be imaged or otherwise processed using techniques known in the art of x-ray inspection. Images obtained using exterior detectors 5 and 6 will emphasize more distant objects 20, whereas images obtained using interior detectors 3 and 4 will emphasize objects 16 nearer the plane of the detectors.

The generalization to a larger number of detectors of the principles described in the foregoing paragraph will readily be apparent to persons skilled in the art of imaging, and is within the scope of the invention as described herein and as claimed in any appended claims.

In accordance with an alternate embodiment of the present invention, one or more collimators 32 may be provided for restricting the field of view of particular detectors, as shown for detector 6, thereby enhancing the selectivity of those detectors in favor of scattering originating at specified depths into enclosure 14.

Figure 2:
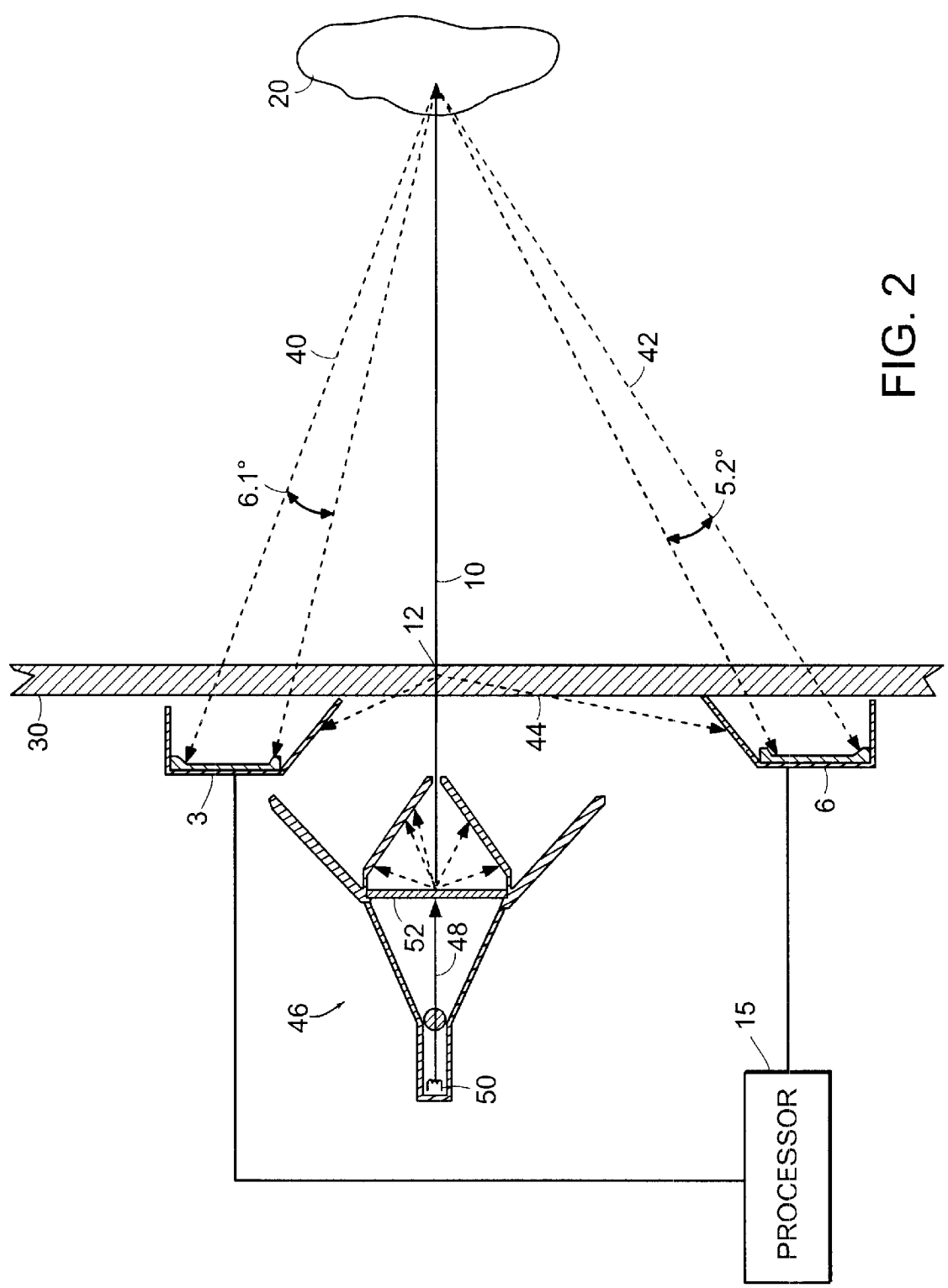
FIG. 2 provides a schematic representation of an x-ray system employing backscatter detectors asymmetrically disposed with respect to an illuminating beam in accordance with a preferred embodiment of the present invention.

Referring to FIG. 2, comparison, by processor 15, of the scattered radiation flux detected at detectors 3 and 6 disposed with lateral asymmetry with respect to beam 10 may advantageously provide a quantitative measure of the distance from the plane of the detectors to scattering object 20 making reasonable assumptions regarding the isotropy of any medium ambient to object 20 through which scattered radiation 40 and 42 propagates to the respective detectors. Scattered radiation 44 scattered from a nearby scattering source 12 may be shielded from detection by one or more of the backscatter detectors 3 and 6.

As shown in FIG. 2, backscatter detectors 3 and 6 are disposed asymmetrically with respect to beam 10. Detector 3 subtends an angle, in the plane shown, of 6.1° with respect to object 20, whereas detector 6 subtends an angle, in the plane shown, of 5.2° with respect to object 20. The further detector 6 gets a fraction less than 1 of the counts recorded by near counter 3. The ratio of counts detected by the respective counters approaches unity as the distance to object 20 increases (as measured with respect to the separation between detectors 3 and 6). In this discussion, it is assumed, for simplicity, that propagation effects with respect to scattered beams 40 and 42 may be neglected. Knowledge of the orientation of beam 10 may allow the location of object 20 to be derived using straightforward algorithms.

An embodiment of source 46 of beam 10 of penetrating radiation is shown. A beam 48 of electrons emitted by cathode 50 is accelerated toward anode 52. Electron beam 48 may be scanned with respect to anode 52 such that the orientation of beam 10 may be varied.

Figure 3:
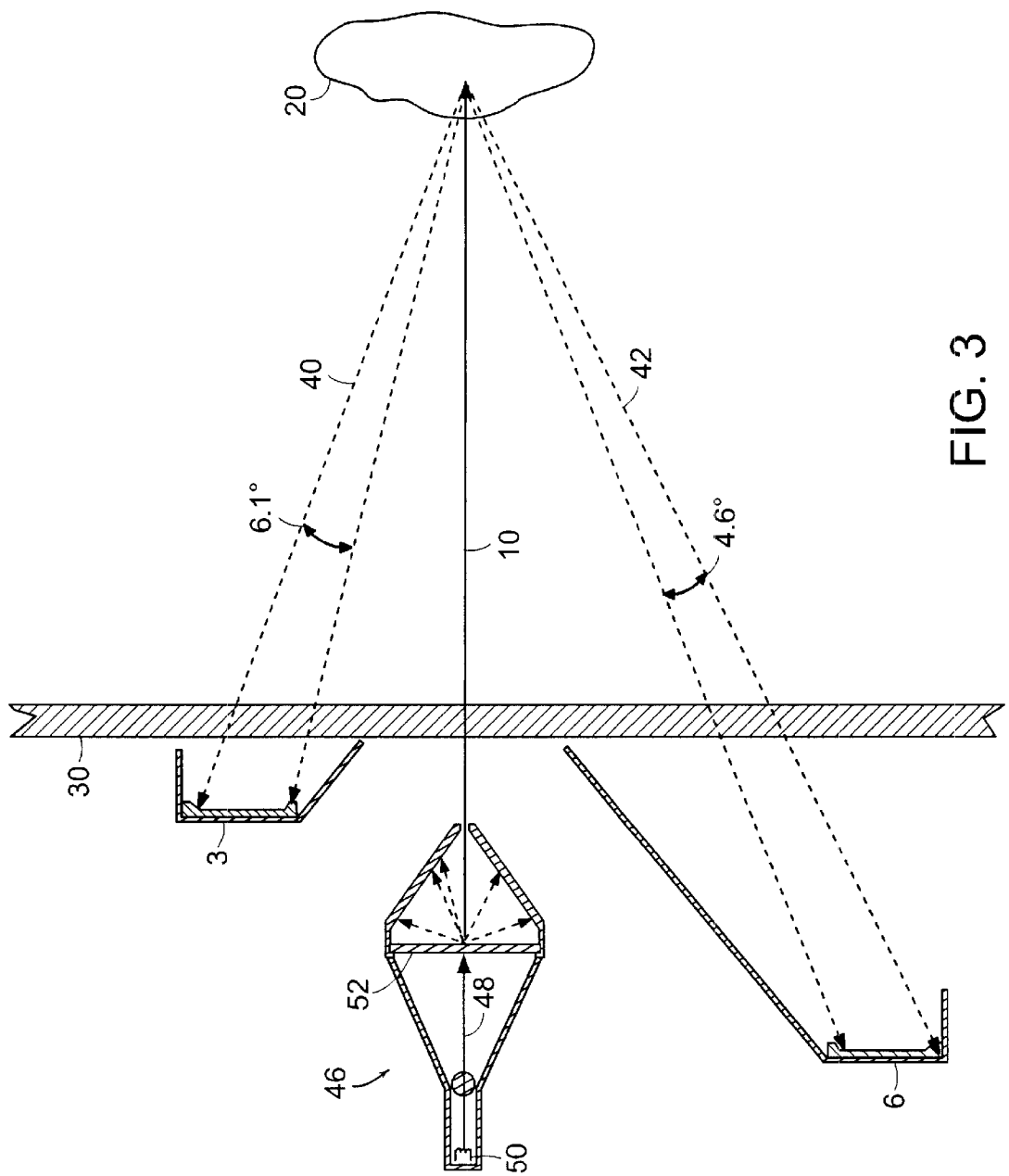
FIG. 3 provides a schematic representation of an x-ray system employing backscatter detectors asymmetrically disposed with respect to an illuminating beam in accordance with a further embodiment of the present invention.

Referring now to FIG. 3, an alternate embodiment of the invention is depicted in which backscatter detectors 3 and 6 are disposed at different distances with respect to concealing surface 30. As discussed with reference to FIG. 2, the difference in counts received by detectors 3 and 6 may be used to determine the distance between concealing surface 30 and scattering object 20. Again, the ratio of scatter flux detected by the respective detectors approaches unity as the distance to scattering object 20 increases.

Figure 4:
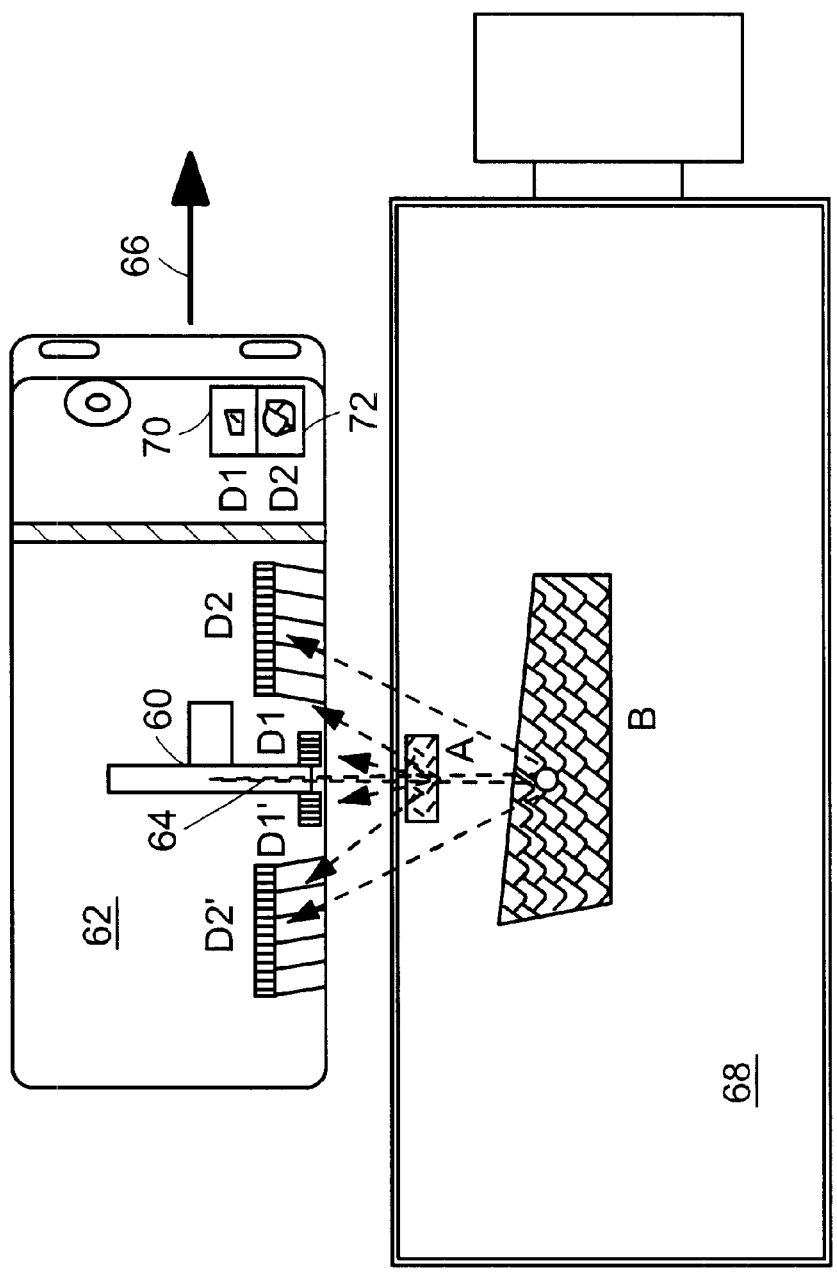
FIG. 4 is a schematic cross-sectional representation of an x-ray system incorporated within a self-propelled vehicle, the x-ray system employing multiple backscatter detectors for obtaining depth information with respect to objects concealed within a large enclosure, in accordance with a preferred embodiment of the present invention.

In accordance with a further alternate embodiment of the invention, a source 60 of scanning x-rays may be mounted on a moving platform such as a self-propelled vehicle 62, as shown in FIG. 4. Source 60 may include a scanning chopper wheel as known in the art for the production of a flying spot beam 64. Vehicle 62 may be driven in direction 66 past a large object 68, such as a truck or sea cargo container, in a manner described in detail in U.S. Pat. No. 5,764,683, which is herein incorporated by reference. Interior backscatter detectors D1 and D1' preferentially detect radiation scattered from near scattering source A, whereas exterior backscatter detectors D2 and D2' preferentially detect radiation scattered from far scattering source B, as described in the foregoing discussion. The respective scatter images derived from interior and exterior detector sets may be displayed, for example, as images on display devices 70 and 72, or otherwise processed as known in the art.

In accordance with other embodiments of the present invention, it is possible to simultaneously measure the effective atomic number of an object, using known techniques, as well as the density of the object so as to give a more precise characterization of the object that can be obtained from each property alone. In some cases, it is possible to reduce or eliminate the effects of the objects geometry with respect to the x-ray source/detector arrangement as well as effects of interposed material.

Transmission of penetrating radiation through the inspected object may also be measured and combined with backscatter data to provide additional characterization of the object concealed within an enclosure. The described embodiments of the invention are intended to be merely exemplary and numerous variations and modifications will be apparent to those skilled in the art. All such variations and modifications are intended to be within the scope of the present invention as defined in the appended claims.

We claim:

1. An inspection system for characterizing an object concealed by a concealing surface, the system comprising:
   a. a source of penetrating radiation for emitting a beam, the beam having an orientation and being incident upon the concealing surface at a plane of incidence, the source having a source position;
   b. a first scatter detector having a specified position with respect to the source position, a beam orientation, and a first field of view, the first field of view subtending a first solid angle, the first scatter detector generating a first signal corresponding to penetrating radiation that has been scattered by the object;

c. a second scatter detector having a second field of view, the second field of view subtending a second solid angle of larger magnitude than the first solid angle, the second scatter detector disposed at a specified position with respect to the source position exterior to the position of the first scatter detector, the second scatter detector generating a second signal corresponding to penetrating radiation that has been scattered by the object; and d. a processor for determining an effective depth of the object with respect to the plane of incidence on the basis of at least the first and second signals.

2. An inspection system according to claim 1, wherein the object subtends a first solid angle with respect to the first scatter detector and a second solid angle with respect to the second scatter detectors such that the first solid angle differs from the second solid angle.

3. An inspection system according to claim 1, wherein the field of view of the second scatter detector is limited by at least one collimator.

4. An inspection system according to claim 1, wherein the source of penetrating radiation is an x-ray source.

5. An inspection system according to claim 1, wherein the source of penetrating radiation is a radioactive x-ray source.

6. An inspection system according to claim 1, further comprising a scanner for moving the propagation axis of the beam of penetrating radiation relative to the object.

7. A method for analyzing an object concealed by a surface, the method comprising:

a. illuminating the surface with a beam of penetrating radiation emanating from a source;

b. detecting radiation scattered by the object by a first and a second scatter detector, the second detector having a field of view subtending a larger field of view than a field of view subtended by a field of view of the first detector, such that radiation scattered by an object disposed at a greater distance from the source of penetrating radiation is preferentially detected by the second radiation detector;

c. generating a first signal corresponding to penetrating radiation scattered by the object and detected by the first scatter detector;

d. generating a second signal corresponding to penetrating radiation that has been scattered by the object and detected by the second scatter detector; and e. determining a position of the object on the basis of at least the first and second signals.

8. A method for analyzing an object concealed within an enclosure, the method comprising:

a. illuminating the enclosure with a beam of penetrating radiation;

b. generating a first signal corresponding to penetrating radiation scattered by the object and detected by a first detector disposed at a first detector position;

c. generating a second signal corresponding to penetrating radiation scattered by the object and detected by a second detector disposed at a second detector position; and d. determining an effective depth of the object on the basis of at least the first and second signals.

9. A device for inspecting a container with penetrating radiation, the device comprising:

a. a bed movable along a first direction;

b. a source of penetrating radiation, mounted on the bed for providing a beam;

c. a first scatter detector disposed at a first detector position for generating a first signal corresponding to penetrating radiation that has been scattered by an object;

d. a second scatter detector having a field of view, disposed at a second detector position, for generating a second signal corresponding to penetrating radiation that has been scattered by the object; such that the beam is caused to traverse the container as the bed is moved, and the first and second signal are used to characterize a distance of the object in a depth direction transverse to the first direction.

* * * * *